United States Patent [19]
Annoni

[11] 3,978,852
[45] Sept. 7, 1976

[54] PLAQUE JACK TOOTHBRUSH

[76] Inventor: Jerry D. Annoni, 41-F Admiral Callaghan Lane, Vallejo, Calif. 94590

[22] Filed: Apr. 7, 1975

[21] Appl. No.: 565,572

[52] U.S. Cl............................ 128/62 A; 15/22 A; 32/50
[51] Int. Cl.²........................................ A61H 7/00
[58] Field of Search .............. 128/62 A, 67, 49, 44, 128/52; 15/22; 32/50

[56] References Cited
UNITED STATES PATENTS

| | | | |
|---|---|---|---|
| 2,044,863 | 6/1936 | Sticht | 128/62 A |
| 2,788,000 | 4/1957 | Lather et al. | 128/62 A |
| 3,159,859 | 12/1964 | Rasmussen | 128/62 A |
| 3,535,726 | 10/1970 | Sawyer | 128/62 A |

FOREIGN PATENTS OR APPLICATIONS

| | | | |
|---|---|---|---|
| 652,626 | 10/1928 | France | 128/62 A |
| 586,675 | 3/1947 | United Kingdom | 128/62 A |

*Primary Examiner*—Lawrence W. Trapp
*Attorney, Agent, or Firm*—Owen, Wickersham & Erickson

[57] ABSTRACT

A powered toothbrush cleans teeth and related embrasures by mechanically driving a small tuft of brush elements axially against the tooth surfaces to remove plaque and into and through the embrasures to push out food particles from the embrasures.

The brush elements in the tuft have a length, texture, density, configuration and/or taper which enable the brush elements (particularly in the central part of the tuft) to penetrate directly into and through the embrasures while retaining sufficient flexibility (particularly on the periphery of the tuft) to effectively scour plaque from both convex and concave tooth surfaces as these brush elements are deflected toward lateral movement along the tooth surfaces by inward driving movement of the brush elements against the tooth surfaces.

The tuft configuration and construction and the axial driving movement of the tuft enable the toothbrush to clean all normal tooth embrasures, regardless of the inclination of the brush handle between verticle and horizontal attitudes; and the size and shape of the tuft enable the brush to be effectively used to clean not only embrasures such as exist between adjacent teeth at the gum line but also crevices in tooth surfaces, the gingival (gum) cuff of both normal and diseased gums, the spaces between orthodontic applicances and teeth, the embrasures existing between bridgework and gums and such normally hard to clean spaces and surfaces as the embrasures between the roots of a tooth resulting from periodontal (gum) surgery.

23 Claims, 18 Drawing Figures

PLAQUE JACK TOOTHBRUSH

BACKGROUND OF THE INVENTION

The present invention relates to a powered toothbrush construction and method for cleaning teeth and related embrasures. It relates specifically to apparatus and methods for cleaning plaque from tooth surfaces and for cleaning embrasures such as the spaces between adjacent teeth at the gum line, the crevices in the molar occlusal surfaces of the teeth, and the gingival (gum) cuff area between the tooth and the gum. It is particularly directed toward hard to reach and clean embrasures and surfaces such as the spaces between orthodontic appliances and the teeth, the spaces between the roots of a tooth and above the gum line as existing after periodontal (gum) surgery, and the spaces between crowns and bridgework and related teeth and gums.

The problems of effectively removing plaque from tooth surfaces (other than from relatively flat, easy to reach tooth surfaces) are well recognized in the dental field. Thus, for example, it is recognized that it is difficult to effectively remove plaque from the tooth surfaces adjacent the gum line and the gingival cuff around each tooth and from those surfaces of the teeth which face adjacent teeth. The conventional manually actuated toothbrush does not properly clean these surfaces.

To get at the surfaces and spaces between adjacent teeth, dentists usually recommend the use of dental floss, but even dental floss has limitations which can mitigate against completely effective use in these areas. For example, dental floss, if used properly, is effective to remove food particles from embrasures existing between adjacent teeth, and it is also effective to remove plaque from convex surfaces where the dental floss can be engaged with a curved surface having this configuration. However, the dental floss will not reach into any concave surfaces or crevices, and therefore cannot remove plaque from such surfaces. It is also difficult to remove plaque from inner (tongue side surfaces) and outer (cheek and lip side) tooth surfaces near the gum line with dental floss. Dental floss also suffers a disadvantage in that the user often does not make the most effective use of it. As a practical matter, dental floss also cannot be used to clean the spaces between orthodontic appliances and teeth or to clean embrasure areas such as those existing between the roots of a tooth and a gum line which has been lowered by periodontal surgery or those embrasure areas existing between a crown or bridgework and an associated tooth or gum surface.

A number of power driven toothbrushes have been designed and constructed in attempts to remedy the limitations of the conventional manually operated toothbrush, but these power driven toothbrushes have not effectively overcome the problem of removing plaque and food particles from many of the problem areas noted above. The power driven toothbrushes developed in the prior art have in most cases been directed toward the concept of reciprocating the toothbrush in a direction generally either along the length or across the width of the brush head in a wiping type of action.

See, for example, U.S. Pat. No. 3,702,487 to Sung, issued Nov. 14, 1972 which shows a mechanized arrangement for aligning the bristles with the tooth striations and moving the bristles in a sweeping brush stroke for brushing from the base of the tooth toward the tip of the tooth. This type of brushing action corresponds with what has been considered to be the preferred dental practice, i.e. brushing along the length of the tooth and away from the gum.

Other motorized tooth brush constructions have been proposed for imparting a vibratory action to the brush head to assist in producing a massaging action of the brush head on the gums. U.S. Pat. No. 1,342,280 to Fitzgerald, issued June 1, 1920 and U.S. Pat. No. 1,703,642 to Sticht, issued Feb. 26, 1929 are examples of such vibratory toothbrush constructions. Each of these patents does produce some endwise movement of the bristles, but the amount of the movement is very restricted, and the brush head is intended to span several teeth so that any benefit that could be obtained by the slight amount of endwise vibratory movement of the bristles is largely dissipated by the damping and bridging effect that the elongated brush head produces as it bridges across several teeth. Each of the Fitzgerald and Sticht patents is primarily directed toward obtaining a slight massaging effect on the gums as the brush head is moved back and forth in its normal brushing sidewise movement.

In contrast, the brush head of the present invention is moved slowly and deliberately across each surface, embrasure, and gingival cuff in order to let the axial movement of the brush elements do the cleaning.

French Pat. No. 870,822, published Mar. 25, 1942 shows a power driven unit that can be used either as a massaging tool for fingernails or as a brush for teeth. In the brush configuration, a rotary brush is mounted for oscillation in a direction parallel to the axis of the brush so that the brush head is driven up and down along the outer (or along the inner) surface of a tooth by the vibrator as the brush is moved manually back and forth along the row of teeth. This is a further example of a power driven brush construction which reflects the more or less accepted dental thinking that the best brushing action is in a direction down the length of the tooth and parallel to the surface of the tooth.

The prior art toothbrushes have therefore not effectively solved the problems of effectively cleaning certain embrasures and related tooth surfaces normally occurring in mouths, e.g. deep crevices in molars, tooth surfaces near the gum line, the gingival cuff area, and the tooth surfaces of embrasures such as exist in the spaces between adjacent teeth above the gum line. Furthermore, the prior art toothbrushes have entirely failed to meet the needs for cleaning such specialized, hard to clean areas as the embrasures existing between crowns and bridgework and the gum, the spaces between orthodontic appliances and teeth, and the spaces between the tooth surfaces of tooth roots extending above the gum line after periodontal surgery. As a good example of the fact that, prior to the present invention, a definite problem existed in the cleaning of such embrasures created by periodontal surgery, it may be noted that some dental techniques suggested inserting pipe cleaners into these spaces to clean out food particles and to help remove some of the plaque build-up.

It is a primary object of the present invention to overcome the problems of cleaning tooth surfaces and embrasures as noted above.

It is a related and an important object to construct a power driven toothbrush and to provide a method of operation which not only prevents plaque build-up, tooth decay and the development of diseased gum conditions, but which also is effective to aid in curing certain diseased gum conditions. In this last regard, clinical evidence has documented that the brush of the present invention has reduced hypertrophied gingival (overgrown gum tissue) in a matter of days.

It is another object of the present invention to construct a powered toothbrush that debilitated persons can use, often without assistance, to do most of the work that is accomplished by dental floss.

It is a further, important object of the present invention to construct a powered toothbrush and to provide a method of tooth cleaning which effects deep cleansing and plaque removal in embrasures and in the gingival cuff with a cleaning action not possible with dental floss or prior art brushes.

SUMMARY OF THE INVENTION

The toothbrush of the present invention is a powered toothbrush and has a brush head which comprises a plurality of elongated brush elements grouped in a relatively small tuft. The tuft has a shape and a length, and the brush elements which make up the tuft have a texture, density, finish, and/or taper flexibility which permit a substantial number of brush elements in the center of the tuft to be driven into an embrasure in an axial direction and with sufficient travel to dislodge food particles from the embrasure while other brush elements in the tuft scour plaque from both convex and concave tooth surfaces as these brush elements are deflected toward lateral movement along the tooth surfaces by inward driving movement of the brush head into the embrasure and toward the teeth.

The toothbrush apparatus and method of operation of the present invention incorporate a number of features which coact to produce a cleaning action effective to clean all parts of the teeth and related gums, bridgework and orthodontic devices. These features include: the relatively small tuft size; the axial mechanically powered thrust of the tuft; the extent of travel of the tuft; and the configuration and composition of the brush elements in the tuft; the way that the brush elements are driven axially into the embrasure space and against the tooth surfaces; and the relationship of the size of the tuft to the embrasures to be cleaned.

In one specific form of the present invention, the tuft has brush elements or different lengths with the longest brush elements positioned at the central part of the tuft. This facilitates cleaning the gingival (gum) cuff area between the gum and the tooth. It also assists in cleaning around diseased gums and related teeth, and it facilitates getting into crevices such as exist on the occlusal (top) surfaces of molars and into small spaces between orthodontic appliances and teeth and between the roots of a tooth and the gum after pariodontal (gum) surgery.

In a particular embodiment of the present invention, the tuft has a diamond shape in plan view and a pyramid shape in elevation view so as to present a generally vertical edge of brush element ends in either the vertical orientation or the horizontal orientation of the brush handle. This, in turn, facilitates using the brush either vertically or horizontally while maintaining a vertical line of bristles aligned with the vertical alignment of the teeth themselves.

The brush is power driven so that the mechanical thrusting of the brush elements axially into the embrasures can be achieved with sufficient power and with sufficient rapidity of stroke to effectively obtain the benefits of this cleaning stroke. Driving the brush elements along their length and axially into the embrasure is much more efficient for dislodging food particles out of the embrasure than wiping the brush elements back and forth along the outer surface which define the embrasure. However, to get the cleaning action and the power required, the tuft must be moved into this embrasure with a certain amount of force, and this amount of force is impractical and in some cases almost impossible to generate manually. The present invention provides an eccentric mechanism for producing this mechanical thrusting of the tuft under power and in an excursion sufficient to produce the desired result.

The present invention also provides a mounting arrangement for detachably mounting the brush head so that brush heads having different tuft configurations can be interchanged for different cleaning application if desired.

Toothbrush apparatus and methods which incorporate the structure and techniques described above and which are effective to function as described above constitute specific objects of this invention.

Other and further objects of the present invention will be apparent from the following description and claims and are illustrated in the accompanying drawings which, by way of illustration, show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the purview of the appended claims.

DESCRIPTION OF THE PREFERRED EMBODIMENTS

A powered toothbrush constructed in accordance with one embodiment of the present invention is indicated generally by the reference numeral 21 in FIGS. 1, 2, 5 and 6.

Figure 6:
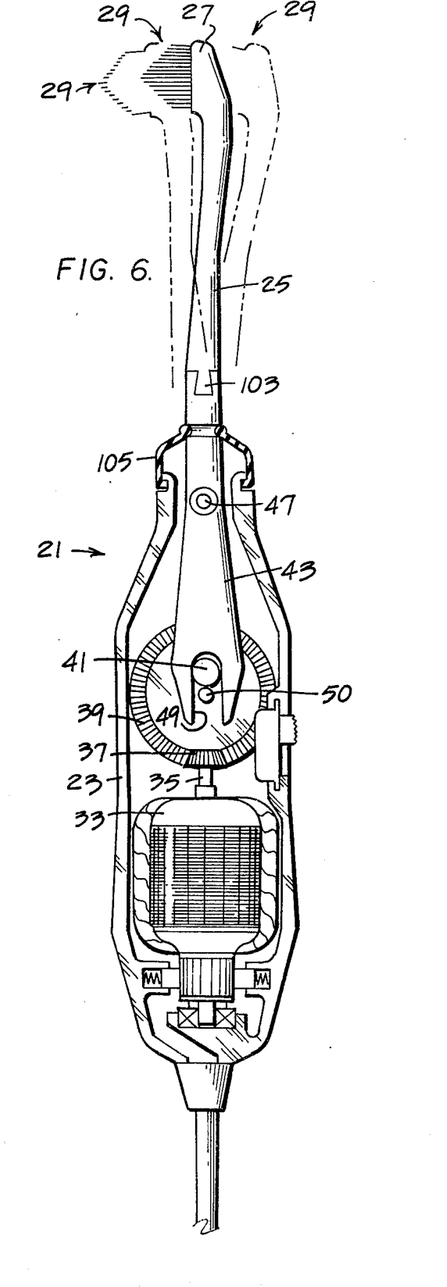
FIG. 6 is a side elevation view, partially broken away to show the details of construction, of the toothbrush shown in FIG. 5.

As best illustrated in the exposed view, the toothbrush comprises (in principle component parts): a housing 23 which serves as a holder; a brush stem member 25; a brush head 27 at the outer end of the stem member 25; a plurality of elongated brush elements 28 (see FIG. 5) grouped in a relatively small tuft 29; and drive means 31 (including a motor 33, a drive shaft 35, gears 37 and 39, an eccentric 41 and a lever 43) for rapidly reciprocating the tuft 29 in an axial direction, as indicated generally by the phantom outlines in FIG. 6.

The lever 43 is mounted for pivoting movement about a pivot 47 (see FIGS. 5 and 6), and the inner end of the lever 43 is bifurcated to provide a slot 49 for engaging the eccentric pin 41. The eccentric offset of the pin 41 with respect to the axis 50 of rotation of the gear 39 and the length of the lever arms of the lever 43 and stem member 25 on opposite sides of the pivot 47 determine the amount of axial reciprocation of the brush head 27 and tuft 29. In preferred embodiments of the invention, this axial travel or excursion is in the range of ¼ inch to ¾ inches, and the individual brush elements 28 in the tuft 29 have lengths in the range of ¼ inches to ⅝ inches. A typical tuft grouping (for a tuft grouping as shown in FIGS. 2–7 and 8–14) will have a long axis of ⅜ inch along the length of the stem member 25 and a width of about ¼ inch across the width of the brush head 27.

Figure 9:
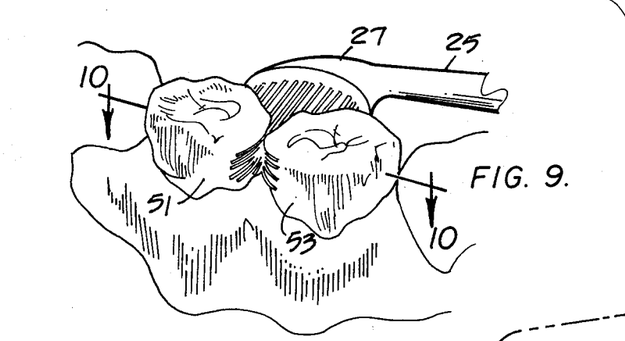
FIG. 9 is an isometric view showing tuft of the toothbrush of the present invention being driven into the embrasure between two adjacent teeth.

The tuft 29 may be formed in a variety of configurations, depending upon the specific application to which the brush is to be primarily directed. For general purpose cleaning of teeth in a normal mouth, the configuration shown in FIGS. 2, 5, 6 and 7 has been found quite acceptable. In this configuration the individual brush elements 28 in the central part of the brush have a somewhat greater length than the other brush elements and the brush elements at the inner and outer periphery of the brush head are the shortest brush elements. All brush elements 28 preferably have polished ends and preferably have a diameter in the range of 0.005 inches to 0.015 inches. These brush elements may also be tapered (from a larger diameter base to a smaller diameter tip) in the range of 0.015 to 0.005 inches. The brush elements can be made of nylon, and in most instances it is preferred to have somewhat stiffer brush elements in the central part of the tuft than around the periphery of the tuft. This tends to facilitate deflection of the peripheral tufts and the desired scouring action of these peripheral elements on the tooth surfaces as the central brush elements are driven into relatively small embrasures, such as the embrasures existing between adjacent teeth 51 and 53 at the gum line as illustrated in FIGS. 9 and 10.

Figure 10:
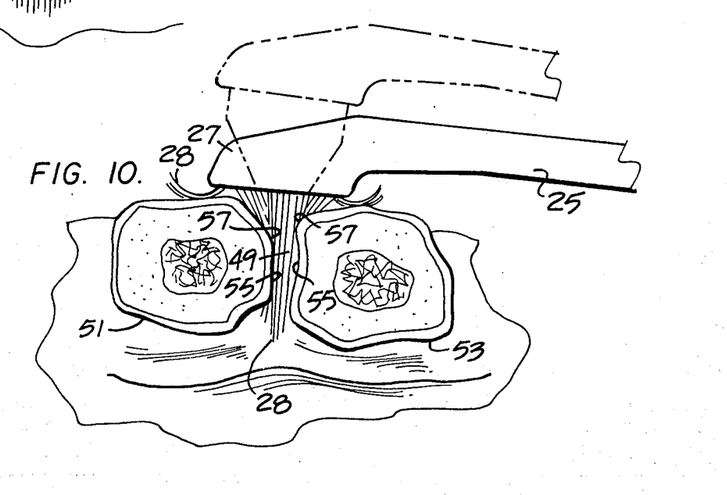
FIG. 10 is a plan view taken generally along the line and in the direction indicated by the arrows 10—10 in FIG. 9 and illustrates how centrally disposed brush elements in the brush head of the present invention are mechanically thrust into and through the embrasure to dislodge any food particles in this space while peripheral brush elements are deflectable to clean and scour plaque from both the convex and concave tooth surfaces adjacent the embrasure.

As best illustrated in FIG. 10, the longer, central brush elements 28 are driven completely through the embrasure 49 existing between the adjacent teeth 51 and 53. As can readily be seen in FIG. 10, the configuration of the tooth surfaces includes both concave surfaces 55 and convex surfaces 57. Dental floss can be used effectively to clean the convex surfaces 57, but it is relatively ineffective to clean plaque from the concave surfaces 55. The flexibility of the individual brush elements 28 together with the way in which these brush elements are driven axially against the tooth surfaces and then deflected along the tooth surfaces together with the rapid and repeated thrusts of the tuft 29 and brush elements 28 against these tooth surfaces produced by the powered drive of the brush effectively scour all of the plaque from all of these tooth surfaces at the same time that the brush elements 28 dislodge and push out any food particles or other foreign matter from the embrasure 49.

Figures 7, 8:
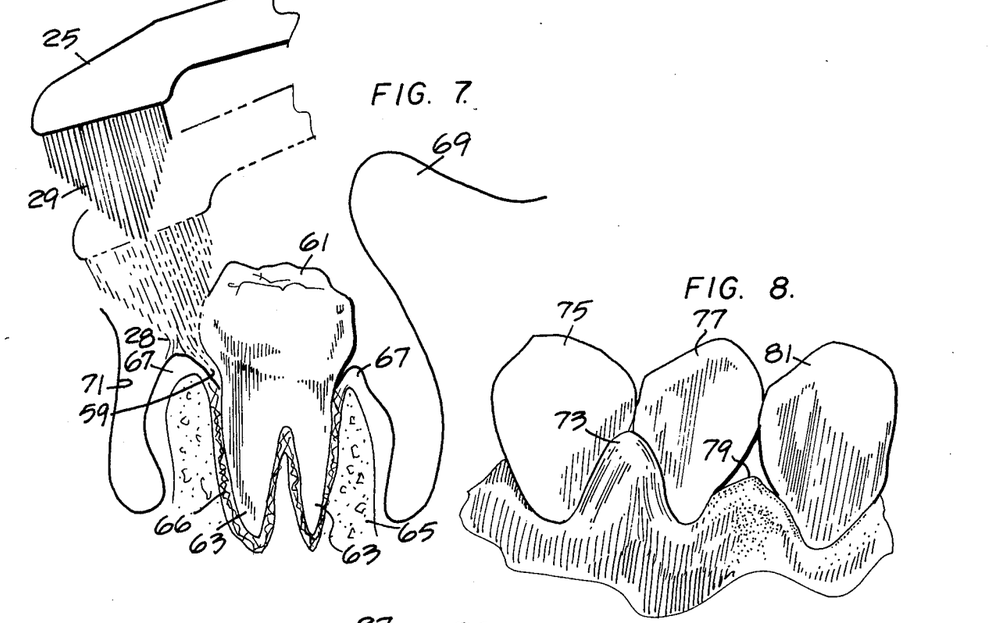
FIG. 7 is a side elevation view showing how the toothbrush and method of the present invention effectively cleans the gingival cuff area around the tooth.
FIG. 8 is a side elevation view of three teeth and related gum showing a typical diseased gum condition between the two teeth on the left and a normal, non-diseased gum condition between the two teeth on the right.

The small tuft 29 and axial drive of the present invention provides a special benefit in that the brush elements 28 can be used to effectively clean the gingival sulcus or gum cuff 59 as illustrated in FIG. 7.

FIG. 7 shows a tooth 61 having tooth enamel on the upper, crown-part of the tooth shown in FIG. 7 and tooth roots 63 extending down into the alveolar bone 65. The periodontal ligament 66 extends between the tooth root 63 and the alveolar bone 65, and the gum 67 extends above the alveolar bone 65 and around the tooth at the level of the lower end of the enamel in the normal, healthy condition of the gum.

The other mouth structure illustrated in FIG. 7 includes the edge of the tongue 69 and the inside surface of the cheek 71.

It is an important feature of the present invention that the tuft 29 and the brush elements in the tuft have a length, texture, density, configuration and/or taper which permit the brush elements to move in and out axially (as illustrated in FIG. 7) of the gingival cuff 59 to clean this area and to remove plaque from the tooth surfaces in this area.

The supra-gingival (above the gum) and sub-gingival (below the gum) concavities which are missed by dental floss are effectively and efficiently cleaned by the brush elements 28 of the present invention.

FIG. 8 illustrates how a diseased gum condition can result in a hyperplastic overgrowth of gum tissue 73 between adjacent teeth 75 and 77. The normal gum configuration is illustrated by the gum condition 79 between the teeth 77 and 81.

With the brush head construction of the present invention, the brush elements enter the diseased gum area 73 perpendicular to the plane of FIG. 8, and the brush elements push and move the diseased gum tissue 73 out of the way. At the same time these brush elements remove plaque from the surface of the tooth 75 and the surface of the tooth 77 and stimulate the gum area encouraging it to recede to the normal formation shown by the healthy gum tissue 79 between the tooth 77 and the tooth 81. This has been documented clinically.

It has also been found that the mechanically powered, specially shaped brush head tuft of the present invention is also effective to stimulate circulation in the gums of diabetics to help firm up the gums. The gums of diabetics have been recognized in the dental field as presenting special problems because of a tendency to bleed and to become inflamed, but the action of the tuft of the present invention in driving the brush elements axially against the gum surfaces has been found to produce the unexpected result of providing a marked improvement in the firmness of such gum tissues.

Figures 11, 12, 13, 14, 15, 16, 17, 18:
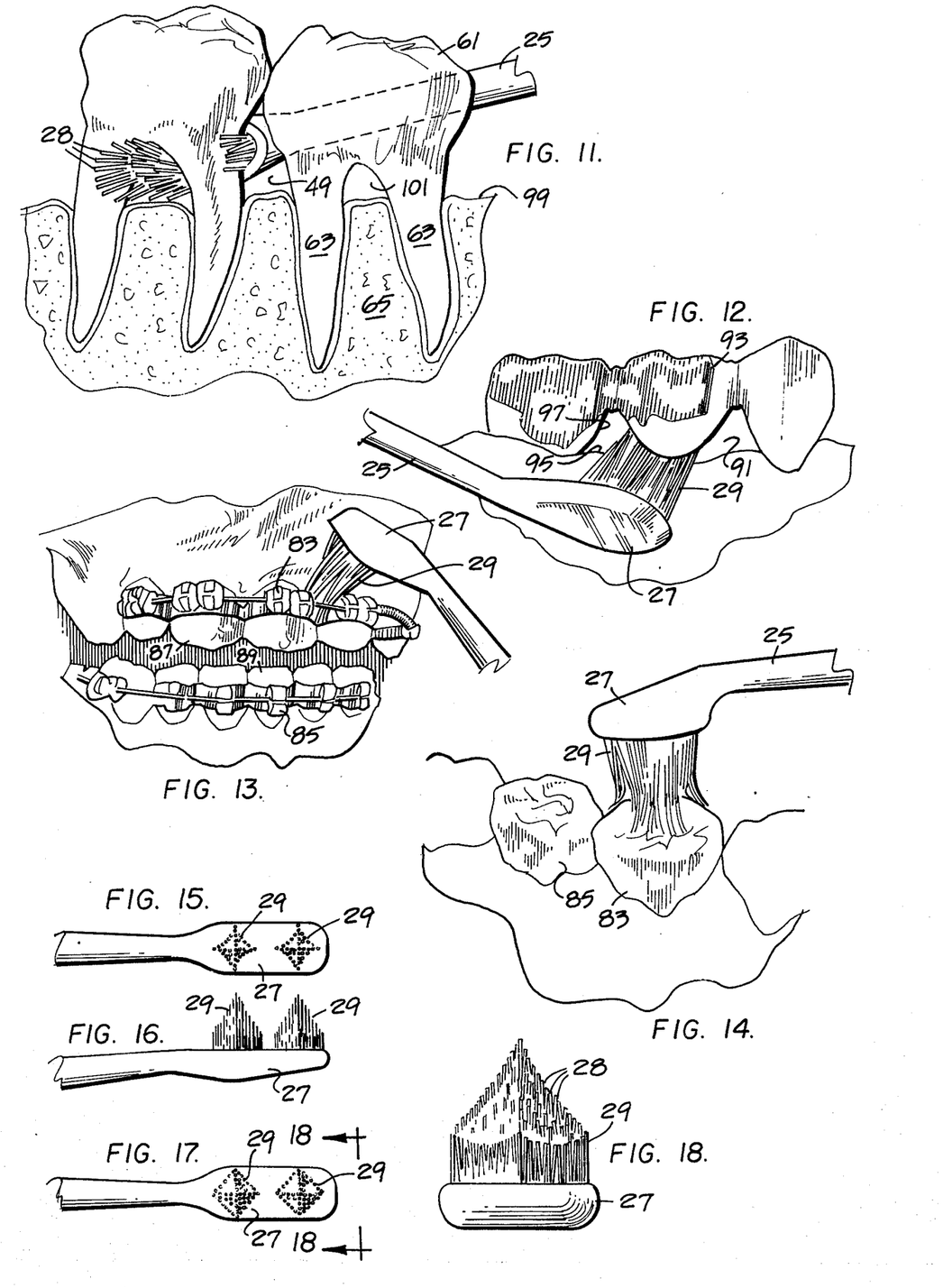
FIG. 11 is an isometric view showing how the brush head configuration and construction of the present invention permits a substantial number of brush elements to be driven into the embrasure existing between the roots of a tooth and above a lowered gum line resulting from periodontal surgery.
FIG. 12 is an isometric view showing how the brush head of the present invention is driven into and through the space between the gum and bridgework to clean this space and related tooth surfaces of this hard to clean area.
FIG. 13 is an isometric view showing how the brush head of the present invention permits brush elements to be thrust into the very small spaces existing between orthodontic appliances and teeth to clean these spaces and the related tooth surfaces.
FIG. 14 is an isometric view showing how the brush head of the present invention permits brush elements to be driven down into deep crevices such as exist in the top and bottom surfaces of molars.
FIG. 15 is a top plan view showing a brush head having two tufts arranged in a star-shaped, diamond configuration in plan view.
FIG. 16 is a side elevation view of the brush head shown in FIG. 15 and illustrates how the tufts have a tent or pyramid shape in side elevation.
FIG. 17 is a view like FIG. 15 but showing a slightly different, diamond-shaped configuration of the tufts.
FIG. 18 is an enlarged end elevation view taken along the line and in the direction taken by the arrows 18—18 in FIG. 17.

Another problem cleaning area is in the deep crevices existing in the occlusal surfaces of molars such as the molars 83 and 85 shown in FIG. 14.

The present invention is particularly useful to clean such crevices. The way in which the individual brush elements 28 are driven axially and perpendicular to the occlusal surface of the tooth and into the crevices, and then deflected off the sidewalls and bottom surfaces of such crevices, provides contact and a proper in-depth cleaning action to all of the exposed surfaces of such crevices. The individual brush elements 28 not only push out any food particles and other foreign matter from the crevices but also, by the deflection produced by driving the brush elements axially and against the surfaces of the crevices, scour all of the plaque from the surfaces.

The impacting stroke of the tuft 29 on the occlusal surface of the molar 83 shown in FIG. 14 is very effective to burnish fluoride in a dentrifice into a tooth surface. This has the effect of polishing or rubbing the fluoride into the tooth and is similar to rolling a roller across a surface a number of times. As a result, less dentrifice is used with the smaller head brush of the present invention and the fluoride is rendered most effective by getting the fluoride down into the pits and fissures of the occlusal surfaces to burnish in the fluoride.

Cleaning between orthodontic appliances and teeth and cleaning the tooth surfaces behind such orthodontic appliances are also recognized problems in the dental field. Dental floss cannot be effectively used in these areas, and the prior art toothbrushes have not been effective to clean these areas because of the wiping rather than the thrusting action of the prior art toothbrushes. The size of the brush head and the relative stiffness and the length of the bristles in the prior art toothbrushes have also prevented effective cleaning in these areas.

Water-pic type apparatus has been used to partially solve this problem of cleaning behind orthodontic braces, but the Water-pic apparatus has limitations in that is is not effective to provide a scouring action to remove plaque from the hard to get at tooth surfaces. At best, it will remove only gross, loose plaque.

As can readily be seen from looking at FIG. 13, the particular tuft configuration of the present invention permits the brush head to be positioned at an attitude in which the brush elements can easily be driven down into and through the spaces between the orthodontic appliances 83 and 85 and the related teeth 87 and 89. The individual brush elements 28 of the tuft 29 penetrate into even the smallest spaces betweeen the appliances and the teeth to dislodge food particles and other foreign matter; and the individual brush elements 29, by virtue of the axial driving action produced by the drive means 31, effectively remove plaque from all nearby surfaces. The relatively small, compact brush head 27 and tuft 29 configuration permit the brush head to be positioned at any angle or attitude required to get in behind the orthodontic braces.

Crowns and bridgework present special problems in cleaning because of the difficulty of reaching the spaces between the bridgework and the gums and adjacent teeth. FIG. 12 shows how the special tuft 29 of the present invention is effectively driven into and through an embrasure 91 existing between a bridge 93 and the gum 95 to clean this space. The brush elements 28 also effectively clean not only the embrasure 91 but also the under surfaces of the bridge 93 and the inner, hard to reach surfaces 97 of the tooth to which the bridge is connected.

In periodontal surgery it is often necessary to cut away diseased gum tissue to an extent such that part of the roots 63 of a tooth extend above the lowered gum line 99. The result is to leave embrasures 101 between the roots of the tooth 61 and the lowered gum line 99, and such embrasures are very difficult to maintain clean with prior art toothbrushes and cleaning devices.

As noted above, one suggested technique has been to use pipe cleaners for cleaning embrasures 101. The configuration of the tuft 29 of the present invention permits the individual brush elements 28 to penetrate into the embrasures 101 to clean this space and also to effectively clean plaque from the exposed surfaces of the roots 63 of the tooth, as illustrated by the action of the individual brush elements 28 in the lefthand side portion of FIG. 11. The result is to produce a cleaning action which effectively solves a problem existing in the prior art.

In each instance the relatively small size of the tuft and the brush head 27, in combination with the powered drive for this brush head, and the other features of the present invention such as the length of the individual brush elements, the extent of axial movement of these elements and the degree of flexibility of these elements, enable effective use to be made of the toothbrush by all kinds of users, including dibilitated users who have difficulty or are unable to use conventional toothbrushes or other cleaning devices such as dental floss.

Figure 1:
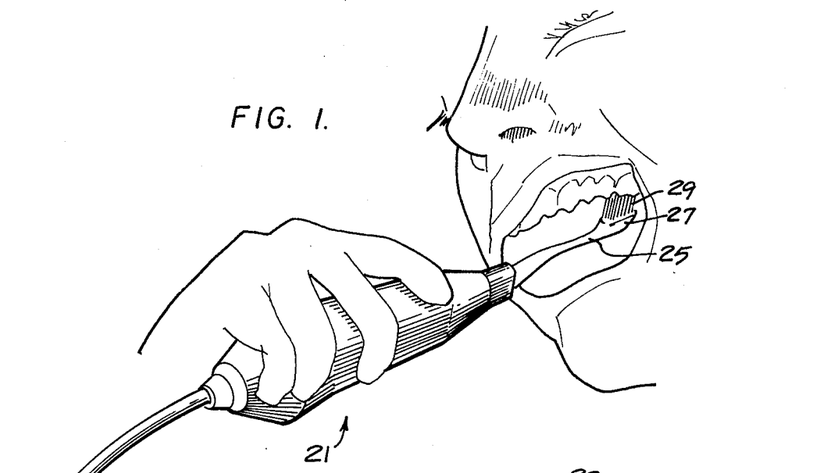
FIG. 1 is a perspective view showing a use of a powered toothbrush constructed in accordance with one embodiment of the invention.
Figure 2:
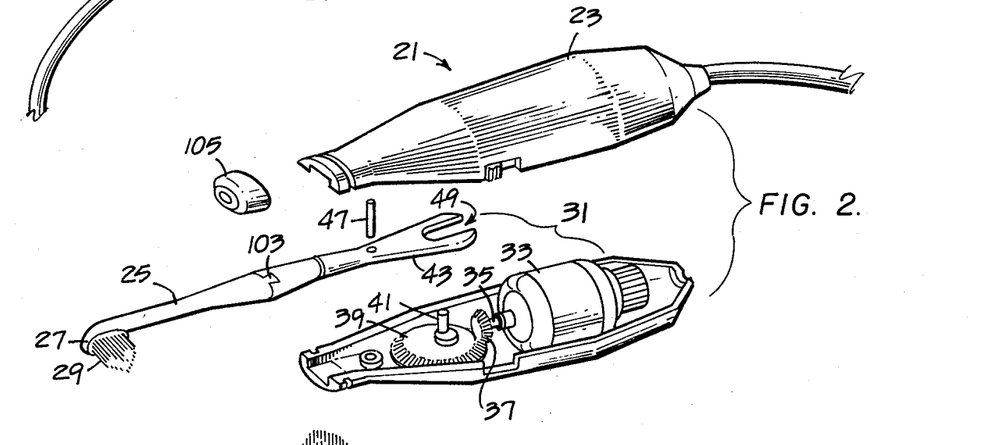
FIG. 2 is an exploded, isometric view of the toothbrush shown in FIG. 1.

At best shown in FIG. 2, the brush stem 25 is detachably connected to the outer end of the lever 43 by a snap-in interlock 103.

The housing 23 is preferably formed of two parts which may be snapped together to provide ease of assembly and disassembly and access to the inner components of the holder 23.

The forward end of the housing 23 is enclosed by a resilient cap 105 which effectively seals out liquids from the interior of the housing while permitting the degree of movement required in this part of the lever 43.

Figure 3:
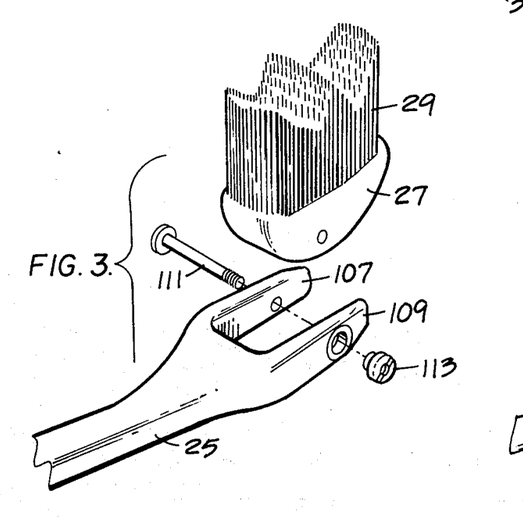
FIG. 3 is an exploded, isometric view showing how a brush head is detachably mounted in one end of the brush stem of the toothbrush.
Figure 4:
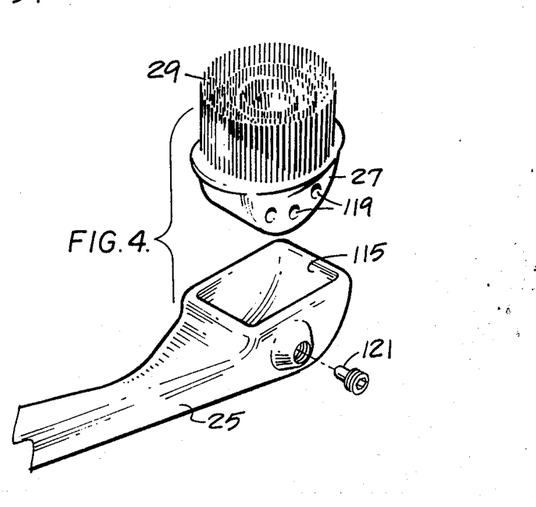
FIG. 4 is a view like FIG. 3 and illustrates a brush head provided with a series of apertures for varying the angle at which the brush head is mounted in the brush stem.
Figure 5:
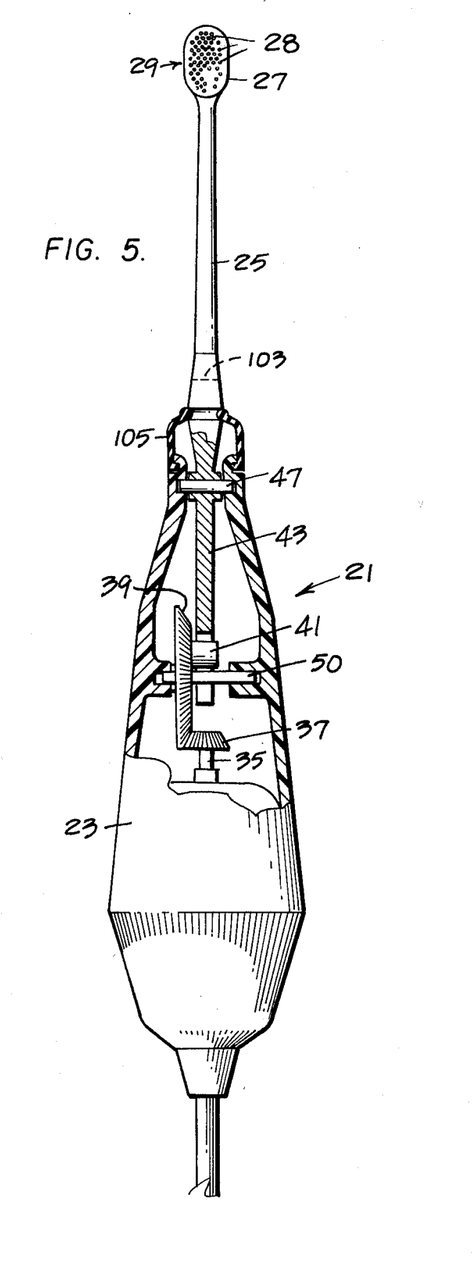
FIG. 5 is a top plan view, partially broken away to show details of construction, of the toothbrush shown in FIGS. 1 and 2.

In some instances it is desirable to provide for interchange of brush heads, and two constructions for doing this are illustrated in FIGS. 3 and 4.

In FIG. 3 the outer end of the stem member 25 has two spaced-apart ends 107 and 109, and a brush head 27 is detachably mounted between these ends 107 and 109 by a bolt 111 and nut 113. The tuft 29 of the brush head 27 in FIG. 3 has a saw-tooth configuration which has specific utility in certain cleaning applications (e.g. removable full and partial dentures).

FIG. 4 shows another modification in which the stem member 25 has a socket 115 at its outer end for mounting a brush head 27. The brush head 27 has a series of spaced openings 119 for permitting the brush head 27 to be mounted at any one of a number of desired angular inclinations with respect to the stem member 25 by insertion of a locking screw 121 through a side wall of the socket 115 and into a selected opening 119.

In the FIG. 4 embodiment the tuft 29 has a generally cylindrical shape with brush elements of substantially uniform length. This flat cut tuft configuration is preferably used in combination with brush elements having more flexibility on the periphery than in the center. This construction shown in FIG. 4 has some advantages for cleaning orthodontic appliances over the diamond-shaped configurations described below.

FIGS. 15–18 show modifications in which two tufts are grouped on a brush head 27.

FIG. 17 shows an arrangement in which the tufts 29 have a generally diamond shape in plan view with the two tufts spaced to accommodate the width of either a single tooth or the width of two teeth. The tufts 29 have a tent or pyramid shape inside elevation (as best seen in FIG. 18), and the individual brush elements 28 provide one ridge of brush elements which runs parallel to the long axis of the stem member 25 and another ridge, in each tuft, that runs transverse to this axis. This construction facilitates alignment of the upstanding ridges with the intertooth spacing, whether the stem 25 is held in a horizontal position or in a vertical position.

The two tufts 29 in the FIGS. 16 and 19 modification are generally diamond-shaped in plan view but are also arranged to provide a generally star shape as shown in FIG. 15. This accentuates the two crossed ridges of individual brush elements extending perpendicularly to one another through the central part of each tuft.

While I have illustrated and described the preferred embodiments of my invention, it is to be understood that these are capable of variation and modification, and I therefore do not wish to be limited to the precise details set forth, but desire to avail myself of such changes and alterations as fall within the purview of the following claims.

I claim:

1. A powered toothbrush for cleaning teeth and related embrasures, such as the spaces between adjacent teeth at the gum line, by driving the ends of specially constructed brush elements axially (along the brush element axes) in and out against the toothed surfaces to remove plaque and into and out of the gingival cuff to clean this area and into and through the embrasures and the space between adjacent teeth to push out food particles from the embrasures and the space between adjacent teeth, said brush comprising, a brush holder, a brush stem member having one end connected to the holder, a brush head at the other end of the stem member, said brush head comprising a plurality of elongated brush elements grouped in a relatively small tuft having a shape and length to permit a substantial number of adjacent brush elements to be driven into and through the embrasures and the space between adjacent teeth, the ends of the brush elements being polished and the brush elements having substantial flexibility for permitting the brush elements to be driven axially into crevices in the tooth surfaces and also into the gingival cuff between the teeth and gums to clean plaque from the tooth surfaces in this area and also to dislodge food particles from the cuff, and drive means in the holder for rapidly reciprocating the tuft in an axial direction and with sufficient travel to permit the brush elements to be driven far enough into the gingival cuff and into and through the embrasures and the space between adjacent teeth to scrub plaque from the tooth surfaces by frictional engagement of the brush elements on the tooth surfaces and to dislodge food particles from the gingival cuff and the embrasures by physical impact of the brush elements on the food particles.

2. The invention defined in claim 1 wherein the tuft has brush elements of different lengths with the longest brush elements positioned at the central part of the tuft.

3. A powered toothbrush for cleaning teeth and related embrasures, such as the spaces between adjacent teeth at the gum line, by driving the ends of brush elements axially (along the brush element axes) in and out against the tooth surfaces to remove plaque and into and out of the embrasures to push out food particles from the embrasures, said brush comprising, a brush holder, a brush stem member having one end connected to the holder, a brush head at the other end of the stem member, said brush head comprising a plurality of elongated brush elements grouped in a relatively small tuft having a shape and length to permit a substantial number of adjacent brush elements to be driven into the embrasures, drive means in the holder for rapidly reciprocating the tuft in an axial direction and with sufficient travel to permit the brush elements to be driven far enough into the embrasures to dislodge food particles from the embrasures, and wherein the tuft has brush elements of different lengths with the longest brush elements positioned at the central part of the tuft, and wherein the brush elements at the periphery of the tuft are less stiff than the brush elements of the central part of the tuft for facilitating deflection of the peripheral brush elements and scouring of plaque from both convex and concave tooth surfaces as the brush elements are deflected toward lateral movement along the tooth surfaces by inward driving movement of the brush head toward the teeth.

4. The invention defined in claim 1 wherein the tuft is generally diamond-shaped in plan and generally pyramid-shaped in elevation.

5. The invention defined in claim 1 wherein the diamond shape has a star configuration plan for presenting a generally vertical edge of brush element ends in either the vertical orientation or horizontal orientation of the brush stem member.

6. The invention defined in claim 1 wherein the brush head comprises two tuft groups and each tuft group has a generally diamond shape plan view and a generally pyramid shape in elevation view.

7. A powered toothbrush for cleaning teeth and related embrasures, such as the spaces between adjacent teeth at the gum line, by driving the ends of the brush elements axially (along the brush element axes) in and out against the tooth surfaces to remove plague and into and out of the embrasures to push out food particles from the embrasures, said brush comprising ,
   a brush holder,
   a brush stem member having one end connected to the holder,
   a brush head at the other end of the stem member,
   said brush head comprising a plurality of elongated brush elements grouped in a relatively small tuft having a shape and length to permit a substantial number of adjacent brush elements to be driven into the embrasures, and
   drive means in the holder for rapidly reciprocating the tuft in an axial direction and with sufficient travel to permit the brush elements to be driven far enough into the embrasures to dislodge food particles from the embrasures, and
   wherein each tuft has brush elements formed with polished ends and longer, stiffer brush elements in the central part of the tuft and softer, shorter brush elements around the periphery of the tuft.

8. The invention defined in claim 1 including a lever mechanism connected to the drive means for reciprocating the tuft axially, said lever mechanism including a lever arm of which the brush stem member forms a part, a pivot connecting a mid-part of the lever arm to the holder, and an eccentric connection between the lever arm and the drive means for producing swinging movement of the lever arm about the pivot and axial reciprocation of the tuft in response to rotational drive by the drive means.

9. The invention defined in claim 8 wherein the lever arm and pivot are constructed to produce at least ¼inch axial reciprocation of the tuft.

10. A powered toothbrush for cleaning teeth and related embrasures, such as the spaces between adjacent teeth at the gum line, by driving the ends of brush elements axially (along the brush element axes) in and out against the tooth surfaces to remove plague and into and out of the embrasures to push out food particles from the embrasures, said brush comprising,
   a brush holder,
   a brush stem member having one end connected to the holder,
   a brush head at the other end of the stem member,
   said brush head comprising a plurality of elongated brush elements grouped in a relatively small tuft having a shape and length to permit a substantial number of adjacent brush elements to be driven into the embrasures, and
   drive means in the holder for rapidly reciprocating the tuft in an axial direction and with sufficient travel to permit the brush elements to be driven far enough into the embrasures to dislodge food particles from the embrasures, and
   wherein the brush head includes a base member mounting the tuft on the base member, the brush stem member is adapted to interchangeably mount different brush head base members at said other end of the stem member and including mounting means for detachably mounting the base member on the other, outer end of the stem member.

11. A powered toothbrush for cleaning teeth and related embrasures, such as the spaces between adjacent teeth at the gum line, by driving the ends of brush elements axially (along the brush element axes) in and out against the tooth surfaces to remove plague and into and out of the embrasures to push out food particles from the embrasures, said brush comprising,
   a brush holder,
   a brush stem member having one end connected to the holder,
   a brush head at the other end of the stem member,
   said brush head comprising a plurality of elongated brush elements grouped in a relatively small tuft having a shape and length to permit a substantial number of adjacent brush elements to be driven into the embrasures, and
   drive means in the holder for rapidly reciprocating the tuft in an axial direction and with sufficient travel to permit the brush elements to be driven far enough into the embrasures to dislodge food particles from the embrasures, and
   wherein the mounting means are constructed to permit the brush head to be mounted at a plurality of selected angles with respect to the brush stem member.

12. The invention defined in claim 1 wherein the brush elements are grouped in the tuft and have lengths, textures, densities and configurations which permit a substantial number of the brush elements to be axially driven between the spaces between adjacent teeth and over and around both normal and diseased gums to stimulate the gums for preventing development of a diseased condition of normal gums and for assisting in eliminating diseased conditions in diseased gums.

13. The invention defined in claim 1 wherein the brush elements are grouped in a tuft having a length, texture, density and configuration which permits the brush elements to pass over and around orthodontic appliances and to clean the tooth surfaces behind and beneath such orthodontic appliances.

14. The invention defined in claim 1 wherein the brush elements are grouped in a tuft having a length, texture, density and configuration which permits the brush elements to be axially driven into the embrasures between the gum and bridgework.

15. The invention defined in claim 1 wherein the brush elements are grouped in a tuft having a length, texture, density and configuration which permits the brush elements to be driven axially into the embrasures between the roots of a tooth and the gum surface resulting from periodontal surgery to remove plaque from these two surfaces and to dislodge any food particles in these embrasures.

16. The invention defined in claim 1 wherein at least some of the brush elements have a taper with a larger diameter in the base portion and a smaller diameter in the tip portion of the brush element.

17. A method of cleaning teeth and related embrasures, such as those existing between adjacent teeth at the gum line, by driving the ends of brush elements against the tooth surfaces to remove plaque and into and through the embrasures and the space between adjacent teeth to push food particles from the embrasures and the space between adjacent teeth, said method comprising, forming a brush head with a plurality of elongated brush elements grouped in a relatively small tuft having a shape and length to permit a substantial number of adjacent brush elements to be driven axially into and through the embrasures and the space between adjacent teeth, rapidly reciprocating the tuft in an axial direction and with sufficient travel to permit the brush elements to be driven far enough into the embrasures to dislodge food particles from the embrasures and the space between adjacent teeth, making at least the brush elements on the periphery of the tuft flexible enough to permit deflection of the peripheral brush elements and scouring of plaque from both convex and concave tooth surfaces as the brush elements are deflected toward lateral movement along the tooth surfaces by inward driving movement of the brush head toward the teeth, and cleaning the gingival cuff by driving the brush elements generally axially into the gingival cuff.

18. The invention defined in claim 17 including cleaning the embrasures between adjacent teeth at the gum line by aligning the tuft generally perpendicularly to the teeth and driving the brush elements axially into and through the embrasure.

19. The invention defined in claim 17 including cleaning the embrasures between orthodontic appliances and related teeth by driving the brush elements axially into and through the embrasures.

20. The invention defined in claim 17 including cleaning embrasures between crowns and bridgework and related teeth and gums by driving the brush elements axially into and through said embrasures.

21. The invention defined in claim 17 including cleaning the crevices in the top and bottom surfaces of molars by driving the brush elements axially into the crevices and wherein the brush elements are sufficiently flexible to deflect and to scour the surfaces of the crevices during axially inward driving movement of the brush elements.

22. The invention defined in claim 17 including stimulating diseased gums by axially driving the brush elements into and against the hyperplastic region of the diseased gums to push the hyperplastic region away from the tooth surface and to stimulate circulation of blood flow in said diseased gums.

23. The invention defined in claim 17 including axially driving the brush elements into the embrasures between the roots of a tooth and a lowered gum line resulting from periodontal surgery to scour plaque from the tooth surfaces in these areas and to dislodge food particles from the embrasures while stimulating the gums by impingement of the brush elements on the gums.

* * * * *